United States Patent [19]
Rayburn et al.

[11] Patent Number: 5,810,855
[45] Date of Patent: Sep. 22, 1998

[54] ENDOSCOPIC DEVICE AND METHOD FOR REINFORCING SURGICAL STAPLES

[75] Inventors: Gary L. Rayburn, Moore, Okla.; Rob G. Riffle, Flagstaff, Ariz.; Frederick J. Walburn, Flagstaff, Ariz.; Benjamin G. Williams, Flagstaff, Ariz.

[73] Assignee: Gore Enterprise Holdings, Inc., Newark, Del.

[21] Appl. No.: 893,438

[22] Filed: Jul. 11, 1997

Related U.S. Application Data

[63] Continuation-in-part of Ser. No. 505,728, Jul. 21, 1995, Pat. No. 5,702,409.

[51] Int. Cl.$^6$ .................................................. A61B 17/04
[52] U.S. Cl. .................... 606/151; 606/220; 227/176.1
[58] Field of Search ........................ 606/151, 213, 606/220, 139; 227/176.1, 19, 180.1; 623/2, 11

[56] References Cited

U.S. PATENT DOCUMENTS

| | | | |
|---|---|---|---|
| 3,079,606 | 3/1963 | Bobrov et al. | 1/120 |
| 3,490,675 | 1/1970 | Green et al. | 227/19 |
| 3,953,566 | 4/1976 | Gore | 264/288 |
| 3,962,153 | 6/1976 | Gore | 260/2.5 R |
| 4,096,227 | 6/1978 | Gore | 264/210 R |
| 4,187,390 | 2/1980 | Gore | 174/102 R |
| 4,354,628 | 10/1982 | Green | 227/19 |
| 4,397,311 | 8/1983 | Kanshin et al. | 227/175.1 |
| 4,520,817 | 6/1985 | Green | 128/305 |
| 4,548,202 | 10/1985 | Duncan | 128/334 C |
| 4,633,861 | 1/1987 | Chow et al. | 128/305 |
| 4,633,874 | 1/1987 | Chow et al. | |
| 4,784,137 | 11/1988 | Kulik et al. | |
| 4,892,244 | 1/1990 | Fox et al. | 227/8 |
| 4,930,674 | 6/1990 | Barak | 227/179 |
| 4,955,959 | 9/1990 | Tompkins et al. | 227/178 |
| 5,014,899 | 5/1991 | Presty et al. | 227/180 |
| 5,040,715 | 8/1991 | Green et al. | 227/176 |
| 5,042,707 | 8/1991 | Taheri | 606/213 |
| 5,203,864 | 4/1993 | Phillips | 606/151 |
| 5,263,629 | 11/1993 | Trumbull et al. | 227/181 |
| 5,346,115 | 9/1994 | Perouse et al. | 227/179 |
| 5,397,324 | 3/1995 | Carroll et al. | 606/139 |
| 5,441,193 | 8/1995 | Gravener | 606/151 |
| 5,503,638 | 4/1996 | Cooper et al. | 623/11 |
| 5,542,594 | 8/1996 | McKean et al. | 227/178.1 |

OTHER PUBLICATIONS

"Wedge Resection of Lung Without Staples on Specimen," Arthur C. Beall, Jr., MD, Javier A. Lafuente, MD, and James W. Jones, MD, PhD, Ann Thorac Surg, 1995;59;1038–46, pp. 1041–1043, copyright 1995 by The Society of Thoracic Surgeons.

"How Prolonged is 'Prolonged Air Leak'?"; Samuel A. Adebonojo, MD; Ann Thorac Surg; 1995;59;544–51 p. 549, copyright 1995 by The Society of Thoracic Surgeons.

"Cystic and Bullous Lung Disease"; M.E. Ribet, MD; Ann Thorac Surg 1992;53: 1147–52; pp. 1147–1150, copyright 1992 by The Society of Thoracic Surgeons.

(List continued on next page.)

*Primary Examiner*—Gary Jackson
*Attorney, Agent, or Firm*—David J. Johns

[57] ABSTRACT

A surgical staple line reinforcement device for use with a variety of surgical staplers having a pivoted connection between stapler arms or jaws, such as endoscopic stapler devices. The device comprises a pair of tubes of bio-implantable material connected together at a hinge. The device can be quickly and easily applied to a surgical stapler by a surgical team to provide tissue reinforcement. The hinged connection of the device provides both for secure attachment of the device to the surgical stapler, and for a barrier to protect the pivot connection from contamination by migrating tissue during operation. Preferably, tear lines are provided on each of the tubes to assist in removing excess material following attachment of staples. The device allows for fast and safe staple reinforcement and rapid stapler separation and removal following installation.

17 Claims, 8 Drawing Sheets

OTHER PUBLICATIONS

"Peri–Strips™ Staple Line Reinforcement—Sleeve Configuration," Care and Handling Instructions, by Bio–Vascular, Inc., Saint Paul, MN, Aug. 94.

"Peri–Strips® Staple Line Reinforcement Sleeve Configuration," Care and Handling Instructions, by Bio–Vascular, Inc., Saint Paul, MN, Nov. 1, 1994.

"Thoracoscopic Laser Ablation of Pulmonary Bullae:" Matthew Brenner, MD, Raouf A. Kayaleh, MD, Eric N. Milne, MD, Luise Della Bella, RN, Kathryn Osann, PhD, Yona Tadir, MD, Michael W. Berns, PhD, and Archie F. Wilson, MD, PhD, Irvine, CA, The Journal of Thoracic and Cardiovascular Surgery, vol. 107, No. 3, Mar. 1994, pp. 883–890.

"Reinforced Staple Line In Severely Emphysematous Lungs"; F.M. Juettner, MD, P. Kohek, MD, H. Pinter, MD, G. Klepp, MD, and G. Friehs, MD, Graz, Austria, J. Thorac Cardiovasc Surg 1989;97:362–3, vol. 97, No. 3, Mar. 1989, pp. 362–363.

"Optimizing Selection of Patients For Major Lung Resection"; Mark K. Gerguson, MD, Laurie B. Reeder, MD, and Rosemarie Mick, MD, Chicago, IL, The Journal of Thoracic and Cardiovascular Surgery, vol. 109, No. 2, Feb. 1995, pp. 275–283.

Median Sternotomy for Bilateral Resection of Emphysematous Bullae:; Oriane Lima, MD, Luis Ramos, MD, Paulo Di Biasi, MD, Luis Judice, MD, and Joel D. Cooper, MD, The Journal of Thoracic and Cardiovascular Surgery, vol. 82, No. 6, Dec. 1981, pp. 892–897.

"The Current Status of Surgery for Bullous Emphysema"; John Connolly, MD and Archie Wilson, MD, the Journal of Thoracic and Cardiovascular Surgery, vol. 97, No. 3, Mar. 1989, pp. 351–361.

"Bilateral Pneumectomy (volume reduction) for Chronic Obstructive Pulmonary Disease"; J.D. Cooper, MD, E.P. Trulock, MD, A.N. Triantafillou, MD, G.A. Patterson, MD, M.S. Pohl, RN, P.A. Deloney, RN, R. S. Sundaresan, MD and C.L. Roper, The Journal of Thoracic and Cardiovascular Surgery, vol. 109, No. 1, Jan. 1995, pp. 106–119.

"Surgical Treatment of Diffuse Emphysema. A Randomized, Prospective Trial of Laser Bullectomy Versus Lung Reduction Surgery with Staples and Bovine Pericardium"; Robert McKenna, Jr., MD, Matthew Brenner, MD, Michael J. Mullin, MD, Narindar Singh, MD, and Michael Berns, PhD, AATS Boston, 1995, p. 176.

"Unilateral Thoracsocopic Surgical Approach For Diffuse Bullous Emphysema"; Robert J. Keenan, MD, Rodney J. Landreneau, MD, Frank C. Sciurba, MD, Peter F. Ferson, MD, Lynda S. Fettermna, MD, Claudia M. Bowers, BSN, and Bartley P. Griffith, MD, AATS Boston, 1995 p. 174.

"Lung Reduction as Bridge to Lung Transplantation in Pulmonary Emphysema"; Marco Zenati, MD, Robert J. Keenan, MD, Rodney J. Landreneau, MD, Irvin, L. Paradis, MD, Peter F. Ferson, MD and Bartley P. Griffith, MD; Ann Thorac Surg, 1995;59:1581–3.

"Effect of Bovine Pericardial Strips on Air Leak After Stapled Pulmonary Resection"; Stephen R. Hazelrigg, MD, Theresa M. Boley, MSN, Keight S. Naunheim, MD, Mitchell J. Magee, MD, Carl Lawyer, MD, Joseph Q. Henkle, MD, Cesar N. Keller, MD; Ann Thorac Surg, Jun. 1997; 63: 1573–1575.

"Prevention of Air Leaks Afte Pulmonary Wedge Resection"; Cecil C. Vaughn, MD, Ernst Wolner, MD, Marcel Dahan, MD, Dominique Grunenwald, MD, Cecil C. Vaughn III, MD, Walter Klepetko, MD, Marc Filaire, MD, Paul L. Vaughn, MD, and Robert A. Baratz, MD; Ann Thorac Surg. vol. 63, 1997.

"Lung Volume Reduction Surgery: Lessons Learned"; Joseph I. Miller, Jr., MD, Robert B. Lee, MD, Kamal A. Mansour, MD; Ann Thorac Surg. 1996;61:1464–1469.

Seamguard Staple Line Reinforcement Material—Recommended Techniques For Thoracoscopic Use, by W.L. Gore & Associates, Inc, Flagstaff, AZ, May 23, 1997.

Brochure—"Breathe Easy: Your Staple Line is Secure" by W.L. Gore & Associates, Inc., Flagstaff, AZ, Aug. 30, 1996.

Brochure—"Histological Comparison of Seamguard Staple Line Reinforcement Material and Peri–Strips" by W.L. Gore & Associates, Inc., Flagstaff, AZ, Oct. 16, 1996.

Advertising Brochure: "Peri–Strips® Staple Line Reinforcement Sleeve Configuration," May 1995, of Bio–Vascular, Inc.

"Peri–Strips(®) Staple Line Reinforcement Sleeve Configuration," Hospital Price Schedule, by Bio–Vascular, Inc., Saint Paul, MN, Nov. 1, 1994.

"Long–Term Results of Surgery For Bullous Emphysema"; Muiris X. FitzGerald, MD, Patrick J. Keelan, MD, David W. Cugell, MD, Edward A. Gaensler, MD, The Journal of Thoracic and Cardiovascular Surgery, vol. 68, No. 4, Oct., 1974, pp. 566–587.

"Anesthesia for Thoracoscopic Laser Ablation of Bullous Emphysema"; Steven J. Barker, PhD,M.D., Chris Clarke, MB,, Narendra Trivedi, MD, John Hyatt, BS, Meg Fynes, BS, Peter Roessler, BS, Anesthesiology, v. 78, No. 1, Jan. 1993, pp. 44–50.

"Surgical Management of Emphysema"; Edward Gaensler, MD, David Cugell, MD, Ronadl Knudson, MD, and Muiris X. FitzGerald, MD, FRCP, FRCPI, Clinics in Chest Medicine, vol. 4, No. 3, Sep. 1983 pp. 443–463.

"Lung Resections Concomitant to Coronary Artery Bypass Grafting"; A. Terzi, G. Furlan, G. Magnanelli, F. Conti, P. Chiavacci, G. Petrilli, N. Ivic, European Journal of Cardiothoracic Surgery, 1994 8:580–584.

ENDOSCOPIC DEVICE AND METHOD FOR REINFORCING SURGICAL STAPLES

RELATED APPLICATIONS

The present application is a continuation-in-part of co-pending U.S. patent application Ser. No. 08/505,728, filed Jul. 21, 1995, now U.S. Pat. No. 5,702,409.

FIELD OF THE INVENTION

The present invention relates to surgical staple devices and means for reinforcing the seams formed by such devices, and particularly to means to reinforce seams formed by endoscopic surgical staple devices.

BACKGROUND OF THE INVENTION

One of the more commercially successful innovations in surgical procedures in recent years is the development of surgical stapler devices. These devices are designed to simultaneously cut and seal an extended segment of tissue in a patient, vastly reducing the time and risks of such procedures. Typically, a surgical stapler comprises two stapler arms, one containing two or more lines of multiple staples and a second containing corresponding means to bend each of the staples into a closed position. For most applications, a surgical blade is included in the device to quickly sever tissue between the lines of staples. Those stapler devices employing a cutting blade are referred to as "anastomotic staplers" and those used without a cutting blade are referred to as "non-anastomotic staplers."

In the operation of a typical anastomotic stapler, the two stapler arms are positioned around tissue to be cut and then locked firmly together. In one motion the surgeon then actuates the stapler device, which simultaneously installs two or more lines of staples through the tissue and cuts a line down the middle of the staple lines. In this manner, the physician can quickly cut and seal up to about 8 cm of tissue at a time. This procedure is much faster than using a conventional process of cutting with scissors or a scalpel and then laboriously sealing the incision with sutures. As a result, patient care is dramatically improved by minimizing bleed time from the surgical site and significantly increasing the speed with which an operation can be completed.

For most procedures, the use of bare staples, with the staples in direct contact with the patient's tissue, is generally acceptable. The integrity of the tissue itself will normally serve to prevent the staples from tearing out of the tissue and compromising the seam before healing has occurred. However, in certain circumstances the tissue that is being sealed is too fragile to securely hold the staples in place. In these instances, the tissue will tend to rip at or near the staple lines, slowing healing and possibly leading to serious complications.

One area where fragile tissue is of particular concern is the use of stapler devices in lung tissue, and especially lung tissue that is affected by emphysema or similar condition. Diseased lung tissue is very fragile and, in extreme cases, will readily tear through unprotected staple lines. With the growing use of surgical staplers in operations on diseased lung tissues such as bullectomies and volume reduction procedures, it has become increasingly important to develop some reliable means to protect fragile tissue from tissue tears due to surgical staples or surgical stapling procedures.

One product that attempts to correct these problems is PERI-STRIPS® staple line reinforcement sleeves available from Bio-Vascular, Inc. of Saint Paul, Minn. This product is specified for use in lung resection procedures in order to buttress the staple lines and help prevent air leakage that can occur through staple holes. The sleeves are of tri-component construction, comprising (1) a thin strip of processed bovine pericardial tissue attached with (2) suture to (3) a section of polyethylene backing material to form a tubular sleeve. These tri-component sleeves are slid over each of the arms of a surgical stapler, with the bovine pericardial tissue carefully positioned on the operative faces of each of the stapler arms.

During an operation, a surgeon staples and cuts through both the bovine pericardial tissue and the patient's lung tissue in order to perform the lung resection procedure. Once the staples are in place, the surgeon must then cut the suture lines holding the bovine pericardial strips in place and remove the polyethylene backing material and sutures.

While the PERI-STRIPS sleeves offer improvement in preventing lung tissue tearing, this product has numerous deficiencies. First, the use of bovine pericardial tissue creates numerous handling problems and costs. This natural tissue must be stored in preservatives (e.g., propylene oxide) before use and the preservatives must be carefully removed through a saline solution wash prior to use. This is viewed as a needless waste of personnel time and effort prior to use of the sleeves. Even after cleaning, the PERI-STRIPS sleeves are required to be kept moist at all times prior to use.

These demanding handling characteristics make it very difficult to quickly employ the PERI-STRIPS sleeves. As a result, it is common that the surgeon will have to waste some of these strips during each operation in order to assure that an adequate number will always be prepared and ready. Since the PERI-STRIPS sleeves are quite expensive, usually constituting one of the most expensive single implements used in a typical lung resection procedure, the need to prepare extra sleeves that may not be used is not a trivial matter.

Another problem with the PERI-STRIPS sleeves is that they are of multiple component construction. The surgeon must exercise particular care that the sleeves are properly aligned prior to stapler actuation and that staples are driven through only the bovine pericardial tissue. Since the polyethylene backing material is not approved for human implantation, it is crucial that only the bovine pericardial tissue is attached to the staple lines and that all of the backing material is removed.

Other concerns with the PERI-STRIPS sleeves include: the need to employ scissors or a scalpel to cut the sutures holding the two materials together; inconsistent product performance due to normal differences in natural animal tissues; difficulties in cutting through the bovine pericardial tissue; and possible contamination or immunological problems where preparation of the PERI-STRIPS sleeves has not been properly performed. Despite all of these constraints, the PERI-STRIPS reinforcement sleeve product remains the primary choice of surgeons performing lung resection procedures.

In an effort to address some of these drawbacks, it has been attempted to form a staple reinforcement device from an artificial implantable material, such as strips of polytetrafluoroethylene (PTFE) cut from vascular grafts or similar devices. The strips of material are held to the operative faces of the stapler arms by loops of suture wrapped around the stapler arms. Once staples are driven through the strip, the surgeon must then cut the suture to free the device from the surgical site. This technique has not been widely employed due to difficulties in preparing, mounting, and using the strips in this form. Additionally, the use of relatively narrow strips of artificial implantable material has a centering problem similar to that encountered with the use of strips of bovine pericardial tissue. In both cases, the strips must be carefully centered on the operative face of the surgical arm or proper staple reinforcement will not occur.

Others have suggested using a reinforcement strip that is attached to the stapler by pins or clips, such as in U.S. Pat. No. 5,542,594 to McKean et al. U.S. Pat. No. 5,441,193 to Gravener teaches use of a resilient film adhered to a stapler anvil in order to accommodate a wider range of tissue thicknesses. While these devices may address some of the handling problems inherent with the PERI-STRIPS product, they have there own deficiencies. The need to use pins, clips, or adhesives to anchor the material in place is not easily performed by either the manufacturer or the surgical staff. Additionally, if the reinforcement strips are preinstalled by the manufacturer, it limits the surgeon's ability to opt to use or not use reinforcement material as he or she deems appropriate.

All of these deficiencies are addressed by the invention disclosed in the parent application. The preferred device of that application employs a sleeve of bio-compatible material that has a rectangular cross-section, providing a slide-on friction fit between the sleeve and the stapler arm. This allows the sleeve to be quickly installed as needed by the surgical staff whenever required without having to use time-consuming mounting means. By constructing the sleeve from a easily handled polymer material, such as polytetrafluoroethylene (PTFE) and especially expanded PTFE, the sleeve requires no special preparation or handling procedures. As a result, the sleeve can be instantly installed on the stapler as needed. Additionally, the sleeve can be provided with tear lines to allow easy separation of excess material once the sleeve is stapled in place.

While the invention of the parent application can also be installed and used on endoscopic staplers, endoscopic staplers have some different requirements from conventional stapler devices. An endoscopic stapler is constructed to allow the stapler to be inserted through a small incision and then operated remotely within a patient's body by the surgeon. To accomplish this, most endoscopic staplers comprise shorter stapler arms (or "jaws") that are connected together on a fixed pivot point in a scissors fashion. The stapler arms are generally mounted remote from the surgeon's actuation means through an extended staff.

This construction presents a number of unique problems. First, it has been found that the scissors-like construction of the stapler arms tends to entrap tissue within the pivot point. This can cause fouling problems within the pivot point. Additionally, the remote nature of the endoscopic stapler can make removal of excess reinforcement material difficult from the surgical site. Finally, secure retention of reinforcement material on remote arms is a major concern for a surgeon.

In light of these problems, it is a primary purpose of the present invention to provide an improved staple line reinforcement material for use on an endoscopic stapler that will fully protect surgical staple lines while being easy to prepare and use.

It is still another purpose of the present invention to provide an improved staple line reinforcement material that addresses problems unique to endoscopic staplers.

These and other purposes of the present invention will become evident from review of the following specification.

SUMMARY OF THE INVENTION

The present invention is an improved device for reinforcing surgical staples for endoscopic surgical staplers. While the present device may be used for a wide variety of surgical procedures using surgical staples, it is particularly suitable for use on fragile tissue, such as lung tissue in lung resection procedures. The device of the present invention is considered an important implement in establishing improved seals of surgical sites, with reduced possibility of tearing or leaks at the surgical sites through or around surgical staples.

The device of the present invention comprises a sleeve adapted to be inserted over a centrally pivoted pair of surgical stapler arms. The sleeve comprises a operative face that extends along each of the stapler arms and also provides a shield over the pivot point connecting the stapler arms. A tubular structure is provided to surround each of the stapler arms to hold the operative face in position on the device. The preferred tubular structure comprises an essentially rectangular cross-sectional dimension that aids in establishing a friction fit between the stapler arms and the sleeve.

The sleeve of the present invention also preferably includes tear lines or other means to allow easy separation of excess sleeve material away from the surgical site after installation of the staples. Additionally, the sleeve may include retention means to aid in removing excess sleeve material from the surgical site. The preferred device is formed from a porous polytetrafluoroethylene (PTFE), and most preferably an expanded PTFE.

The sleeve of the present invention is far easier to prepare and use on an endoscopic surgical stapler than previous staple reinforcement devices. Additionally, the unique construction of the sleeve of the present invention allows the endoscopic stapler to function more effectively than has previously been possible.

BRIEF DESCRIPTION OF THE DRAWINGS

The operation of the present invention should become apparent from the following description when considered in conjunction with the accompanying drawings, in which.

DETAILED DESCRIPTION OF THE INVENTION

The present invention is an improved device for use in reinforcing staple lines created by a surgical stapler.

Figure 1:
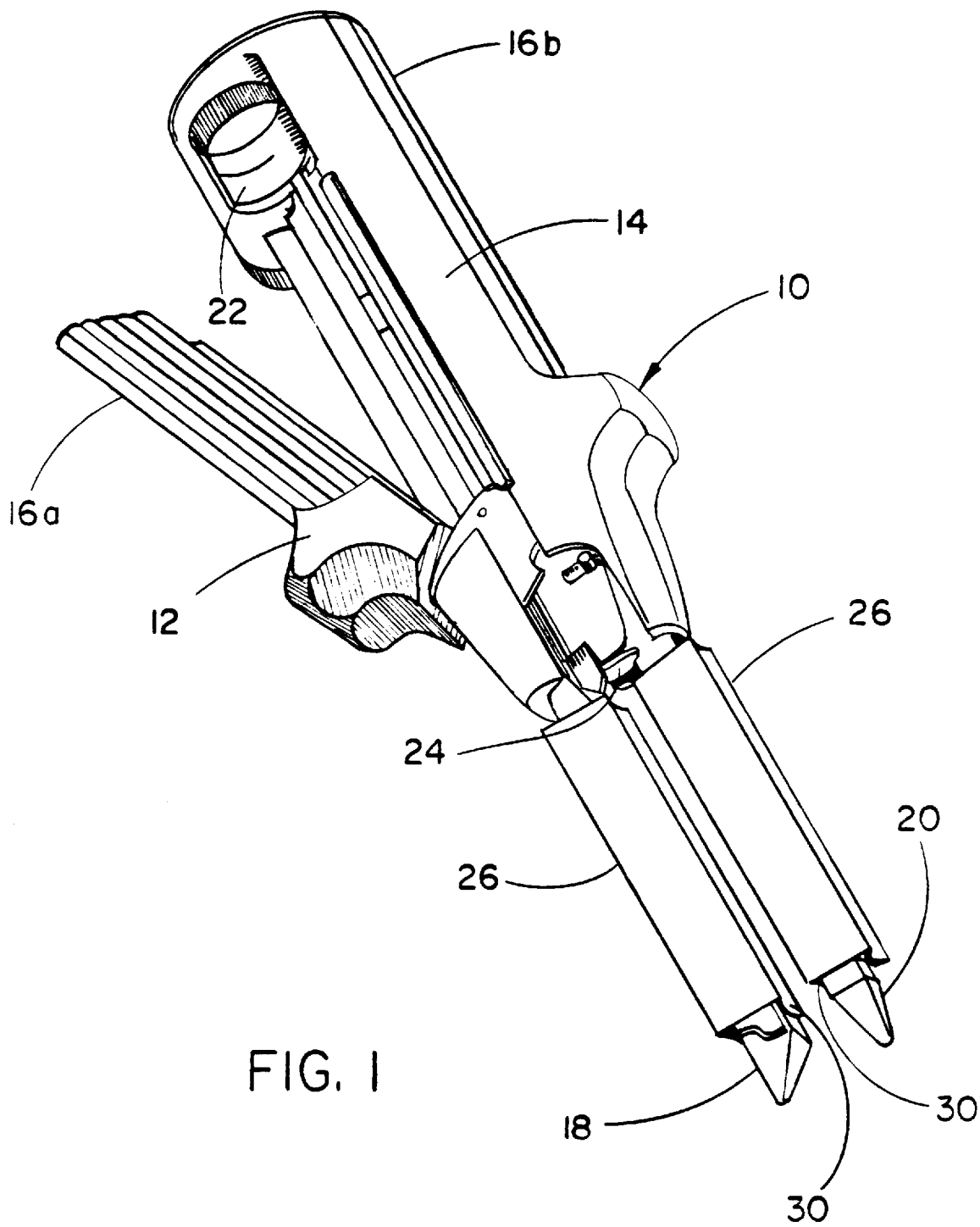
FIG. 1 is a perspective view of a surgical stapler having two surgical staple reinforcement devices of the present invention mounted on its stapler arms.

Shown in FIG. 1 is a conventional surgical stapler 10. The stapler 10 comprises two separate halves 12, 14 that can be locked together. Each of the halves 12 and 14 has its own handle 16a and 16b, respectively, allowing manipulation of the stapler. On the first half 12 is a first stapler arm 18 that is loaded with one or more rows of surgical staples. A corresponding second stapler arm 20 is on the second half 14, containing means to bend each of the staples contained in the first stapler arm 18 into a closed position. This means to bend the staples usually comprises a series of contoured grooves, each corresponding to one of the staples contained in the first stapler arm 18. Finally, one of the halves contains an actuation arm 22 that fires each of the staples. In an anastomotic stapler device, the actuation arm 22 both fires the staples and actuates a cutting blade 24. The cutting blade 24 is oriented between at least two rows of staples, allowing each row of staples to seal on either side of the cutting blade simultaneously with the cutting action.

In operation, the two halves 12, 14 of the stapler 10 are locked together with each of the stapler arms 18, 20 positioned on either side of tissue to be sealed. Once the surgeon assures that the arms 18, 20 are properly positioned, the actuation arm 22 is moved forward, firing the staples and sealing the surgical site. In an anastomotic stapler device, the staples are fired simultaneously with the slicing the tissue with cutting blade 24. The result is a rapid and accurate cutting and sealing of a patient's tissue that is much faster than previous cutting and suturing techniques.

As has been noted, while commercially available staplers function well for most cutting and sealing applications, problems have been experienced with the placement of staples in relatively weak and fragile tissue, such as the lung tissue of emphysema patients. The need for some form of staple reinforcement has been recognized, but until the present invention no fully adequate staple reinforcement device has been available.

Figure 2:
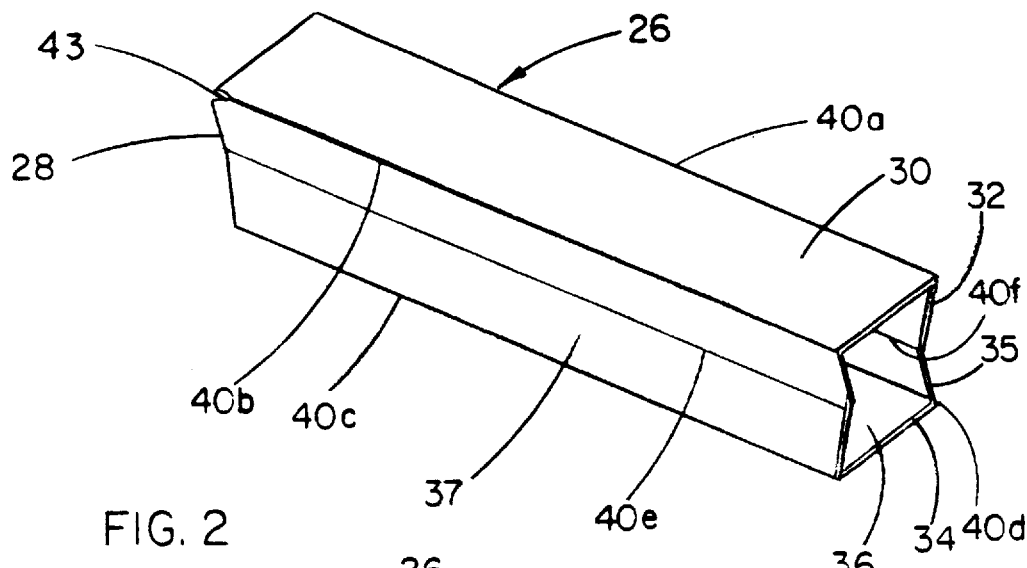
FIG. 2 is a three-quarter isometric view of one embodiment of a surgical staple reinforcement device of the present invention.

In the present invention a staple reinforcement device is provided that overcomes many of the problems previously experienced with such devices. A first embodiment of the staple reinforcement device 26 of the present invention is shown in FIGS. 1 and 2. This device 26 comprises a sleeve 28 having at least one face 30 adapted to receive the rows or lines of surgical staples and at least one side/back wall 32 adapted to surround the stapler arms 18, 20 and hold the device 26 in place. An opening 34 is provided on at least one end of the sleeve 28 to allow installation of the sleeve over the stapler arms.

Unlike some previous tubular staple reinforcement devices, the device of the present invention is formed entirely from an implantable material. This allows the device to be mounted and used with substantially less care than previous staple reinforcement devices. For instance, a slight misalignment of the device will never result in the accidental attachment of non-implantable material within the patient or an inadequate amount of reinforcement material protecting the tissue.

In the embodiment of FIGS. 1 and 2, the wall 32 comprises essentially three other operative faces 35, 36, and 37. This construction allows any one of the faces 30, 35, 36, or 37 to receive and reinforce the staples in a patient's tissue. As a result, less care and manipulation is required by the surgical team to mount and center the sleeve prior to use.

Preferably, the device 26 is constructed from porous polytetrafluoroethylene (PTFE), and particularly a stretched or expanded PTFE such as that made in accordance with U.S. Pat. Nos. 3,953,566, 3,962,153, 4,096,227, and 4,187,390, all incorporated by reference. By heating and rapidly expanding PTFE in accordance with the teachings of these patents, the resulting material exhibits exceptional strength in the direction that it has been expanded.

PTFE, and particularly expanded PTFE, has numerous properties that make it particularly suitable for use as an implantable material. First, the material is highly inert, sterilizable, and bio-compatible. As a result, it is widely employed as vascular grafts and various other implantable tube and sheet materials. Further, PTFE has extremely low coefficient of friction, which allows the material to slide easily onto and off of the stapler arms 18, 20 as well as being easily and smoothly cut by the cutting blade 24 and sealed by the surgical staples. Finally, expanded PTFE material can be selectively expanded to have exceptional strength where needed to resist staple pullout and to have ready severability in the direction of cut of the device.

The preferred sleeve of expanded PTFE for use with the present invention is formed in the following manner. A fine powder PTFE resin is blended with a lubricant, such as odorless mineral spirits, until a compound is formed. The volume of lubricant used should be sufficient to lubricate the primary particles of the PTFE resin so as to minimize the potential of the shearing of the particles prior to extruding. The compound is then compressed into a billet and extruded, such as through a ram type extruder, to form a coherent extrudate. A reduction ratio of 30:1 to 300:1 may be used (i.e., reduction ratio =cross-section area of extrusion cylinder divided by the cross-section of the extrusion die). For most applications a reduction ratio of 75:1 to 150:1 is preferred. The lubricant may then be removed, such as through volatilization. If desired, the extruded product may then be further expanded in at least one direction 1.1 to 50 times its original length. Expansion may be accomplished by passing the dry coherent extrudate over a series of rotating heated rollers or plates. A tube can be stretched in a hot oven to maintain its tubular structure.

Finally, the product should be heat set (also referred to as "amorphorously locked") to retain the material in its final expanded condition. This may be accomplished by exposing the material to a heat of about 327° to 380° C. for about 25 seconds to about 4 minutes or more.

To form a tubular structure for use as the present invention, it is preferred that the extrusion step occur through a circular, semi-circular, triangular, rectangular, or other closed ring die so as to deliver a tubular product. The die should be proportioned so that the final product will fit snugly over the desired stapler arms.

Alternatively, the tubular structure can be formed by creating a sheet or tape of the expanded material and then wrapping the sheet or tape into a tubular form. This can be accomplished through any suitable means, such as longitudinally wrapping (i.e., in a "cigarette" wrap fashion) or helically wrapping (e.g., over a mandrel or similar structure). The wrapped product may be bonded to itself by adhesive, heat bonding, mechanical means (e.g., a suture seam) or similar means to form a sleeve that will attach over the stapler arms. It should be understood that it is contemplated by the present invention that small amounts of materials such as adhesives or suture may be used to bind the tubular structure together without departing from the intend scope of the present invention.

Without intending to limit the scope of the present invention, the final product preferably comprises an expanded PTFE structure with the following range of properties: an expansion/stretch ratio of 2:1 to 6:1 or more (e.g., 10:1); a fibril length of about 2 to 90 micron; a longitudinal strength of above about 10 kg; a transverse strength of above about 5 kg; a density of about 0.8 to 1.5 g/cc; and an average wall thickness of about 0.125 to 2.5 mm.

Each of these properties may be measured in a conventional manner. Fibril length may be determined by the mean length of the fibrils extending between nodes of a sample of the expanded PTFE material measured on a scanning electromicrograph (SEM) of the sample. Longitudinal and transverse strength may be determined through use of a tensile strength tester, such as an INSTRON tensile tester available from Instron Corporation. Density may be determined by dividing the measured weight of the sample by the computed volume of the sample. Average wall thickness may be determined through conventional means, such as through the use of calipers or measurements from SEMs.

Material suitable for use in the present invention is commercially available in a number of forms. For instance, tubular structures of expanded PTFE that may be modified for use on surgical stapler arms are commercially available from W. L. Gore & Associates, Inc., Flagstaff, Ariz., in the form of prosthetic vascular grafts under the trademark GORE-TEX®. Additionally, sheets and tapes of expanded PTFE material that may be constructed into the sleeves of the present invention are commercially available in a wide variety of forms from a number of sources, including W. L. Gore & Associates, Inc., Elkton, Md., under the trademark GORE-TEX®.

Although not preferred, other possible implantable materials that may be employed with the present invention include: nylon; polypropylene; polyurethane; silicone; DACRON® polymer; etc. For some applications, it may be desirable to use a bio-absorbable implantable material, such as polyglycolic acid (PGA), polylactic acid (PLA), polycaprolactone, or natural animal membranes.

It is particularly preferred that the device of the present invention includes means to allow separation of the attached face of the sleeve from the remainder of the sleeve following actuation of the stapler. This can be accomplished in any one or more of a number of ways. The tubular structure of the sleeve may be modified during its formation to selectively weaken certain areas so that they will readily rip longitudinally. Where sleeve is being created by extrusion, this can be accomplished by modifying the extrusion die to reduce the thickness of the sleeve in certain areas to create tear lines. For instance, one or more projections may be provided into the flow of extrudate passing through the die that will reduce the thickness along longitudinal lengths of the tubular structure being produced. These longitudinal lengths will thereby be weakened, allowing the material to more readily separate (or "tear") along these lengths. Any structure that will provide for controlled separation of material in this manner is referred to herein as a "tear line."

One example of tear lines is shown in FIG. 2. In that embodiment, the tube being extruded has an essentially rectangular cross-section, with a wall thickness of about 0.125 to 1.0 mm, with about 0.375 to 0.8 being a typical thickness. If desired, the wall thickness may be increased up to about 2.5 mm for use with most current stapler devices. By modifying the corners of the die extruding this tube, the wall thickness in corners can be reduced by about 25 to 75%, with a preferred reduction being about 65%. This produces four tear lines 40a, 40b, 40c, 40d running the length of the sleeve. When a transverse tension is applied to the sleeve, separation of material will readily occur along the tear lines and the separation will easily propagate along the length of the tube to allow the backing material to be removed from an attached face. For example, with the attachment of face 30, separation of backing material 32 can be accomplished by tearing along tear lines 40a and 40b.

For further ease in separation, small cuts 41 may be provided at an end of the tear lines 40 to ease in starting the tear propagation. The cut 41 may be provided by the surgical personnel before or after actuation of the stapler. Alternatively, the cut 41 may be supplied on the sleeve by the sleeve manufacturer.

It should be appreciated that the tear lines 40 may be provided at any desired location on the sleeve to address particular needs. For example, in the embodiment of FIG. 2, two folds are provided longitudinally on faces 35 and 37. Tear lines 40e and 40f may alternatively or additionally be provided along these folds to provide different or increased options for separating the sleeve following installation.

Another method of creating tear lines is to produce the tear lines following creation of the sleeve. This can be accomplished by stripping or modifying the sleeve material in the places where tears are desired, such as through: selective heating or altering of the sleeve material to create the tear line (e.g., through use of a laser or heated cutting implement); cutting the sleeve to a prescribed depth along the desired tear line (e.g., with a cutting blade); mechanically altering the material (e.g., through use of pinch rollers); selectively weakening the material; etc.

Alternatively, the sleeve may be scored with lines of holes or similar structures that will provide sufficient weakening to allow easier separation of remainder portions of the sleeve following installation. This can be accomplished through a number of means, such as: creating holes with lasers; punching holes; using a pinch roller with teeth; etc.; or through some combination of any of the methods described.

Figure 5:
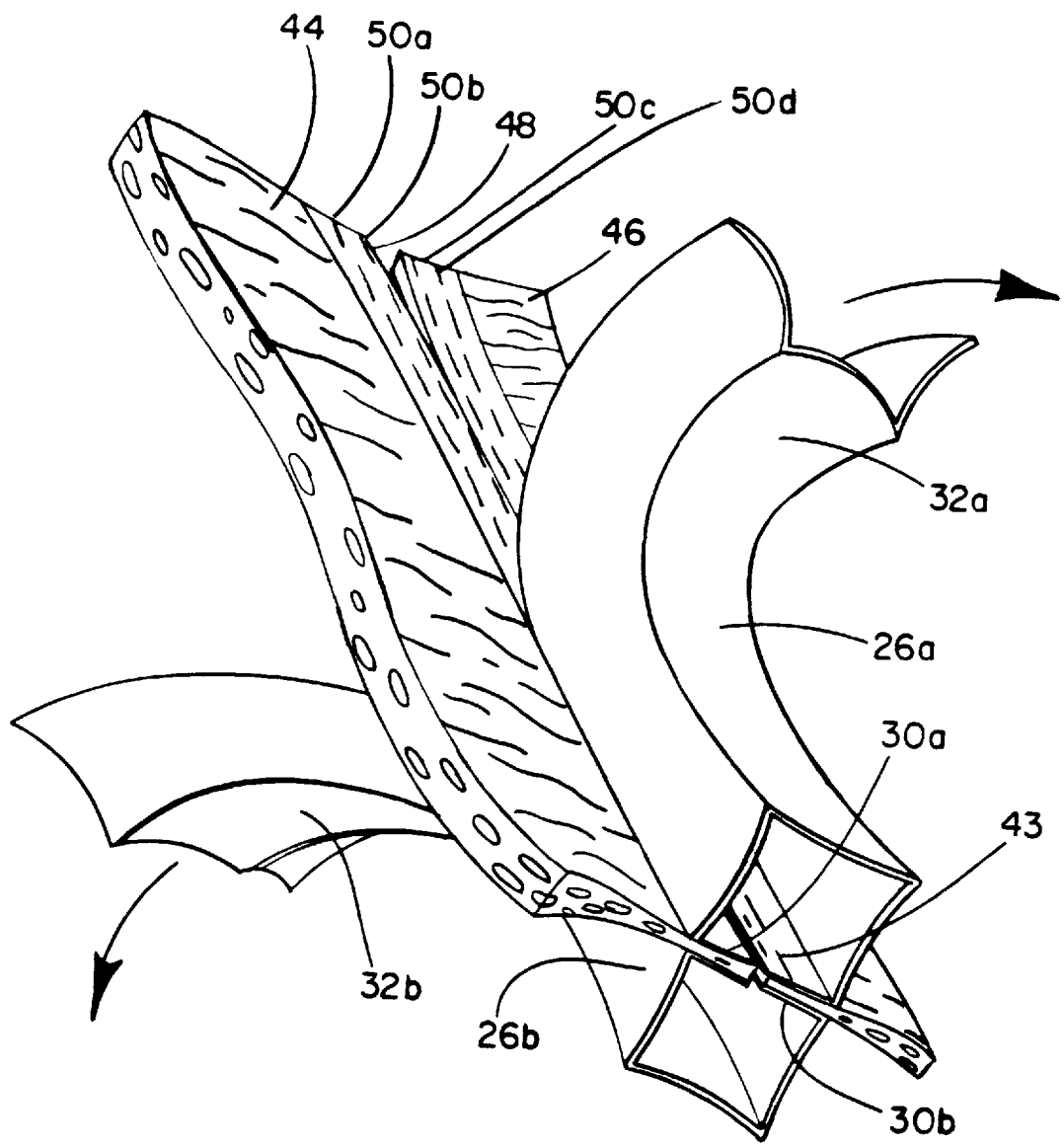
FIG. 5 is a perspective view of two surgical staple reinforcement devices of the present invention shown attached to either side of tissue immediately following actuation of the stapler device, with the reinforcement devices shown partially separated and with the stapler not shown for clarity.

Once tear lines are created, separation of material following installation can be easily and rapidly accomplished. Shown in FIG. 5 is one example of two devices 26a, 26b of the present invention essentially of the construction shown in FIGS. 1 and 2. As is shown, the devices 26a, 26b are attached by staples 43 to two segments of tissue 44, 46 along faces 30a and 30b. The tissue segments 44, 46 have been cut from one another along incision line 48 using a anastomotic surgical stapler and sealed by staple lines 50a, 50b, and 50c, 50d, respectively.

Once the stapler has been actuated, cutting and sealing the tissue, the backing material 32 of each of the sleeves can be separated from attached faces merely be ripping along tear lines 40a and 40b. This is normally done with the stapler arms still in place around the cut site. In the illustration of FIG. 5, the surgical stapler is not shown at the cut site so as not to obscure details concerning the surgical cut 48 and the placement of the staples 43. As is shown, once the backing material 32a, 32b is removed, only the operative faces 30a, 30b of the sleeves are left in place.

The provision of tear lines that readily separate the stapler from the attached reinforcement material is considered to be an extremely useful attribute of the present invention. Previous sleeve devices required some form of cutting of attachment sutures or similar action to release an applied staple reinforcement device from its backing material and the stapler itself. This is an extra step for the surgeon, but may not be particularly burdensome for many operative procedures where there is unobstructed access to the surgical site.

However, with the growing use of endoscopic surgical procedures, with their intentionally limited access to the surgical site, the need to perform an additional cutting step in order to separate a stapler from staple reinforcement material can be quite burdensome. In fact, the presence of non-implantable material attached to the staple reinforcement material, such as that present with the PERI-STRIPS reinforcement materials, raises even more concerns for the surgeon who must be assured that all such material is completely removed from the endoscopic surgical site before terminating the procedure. If multiple staple lines are being installed, this increases the risks even more for the surgeon that non-implantable material may be accidentally attached to the surgical site. With each of these problems, the endoscopic surgeon must address these concerns with severely restricted space and tools.

The reinforcement device of the present invention avoids all of these problems. First, the fact that the device is made entirely from implantable material assures the surgeon that non-implantable material will not be accidentally attached to the patient. Second, the provision of tear lines allows the surgeon to easily separate the stapler from the surgical site with little or no additional cutting procedures. In fact, it is preferred that the tear lines are proportioned so that the mere action of separating the stapler arms from one another will completely cut the tear lines and allow removal of the stapler from the surgical site. Excess portions of the reinforcement device can then be removed by forceps or similar method.

Further, particularly for endoscopic procedures, it is contemplated that means may be provided on the stapler device to aid in the extraction of excess reinforcement material following automatic reinforcement device separation. For example, the reinforcement material may be adhered to the stapler through mechanical means (e.g., clips, tether lines, etc.), pressure sensitive adhesive strips, etc. In this manner, excess reinforcement material can be withdrawn from the surgical site automatically along with the stapler.

Figure 6:
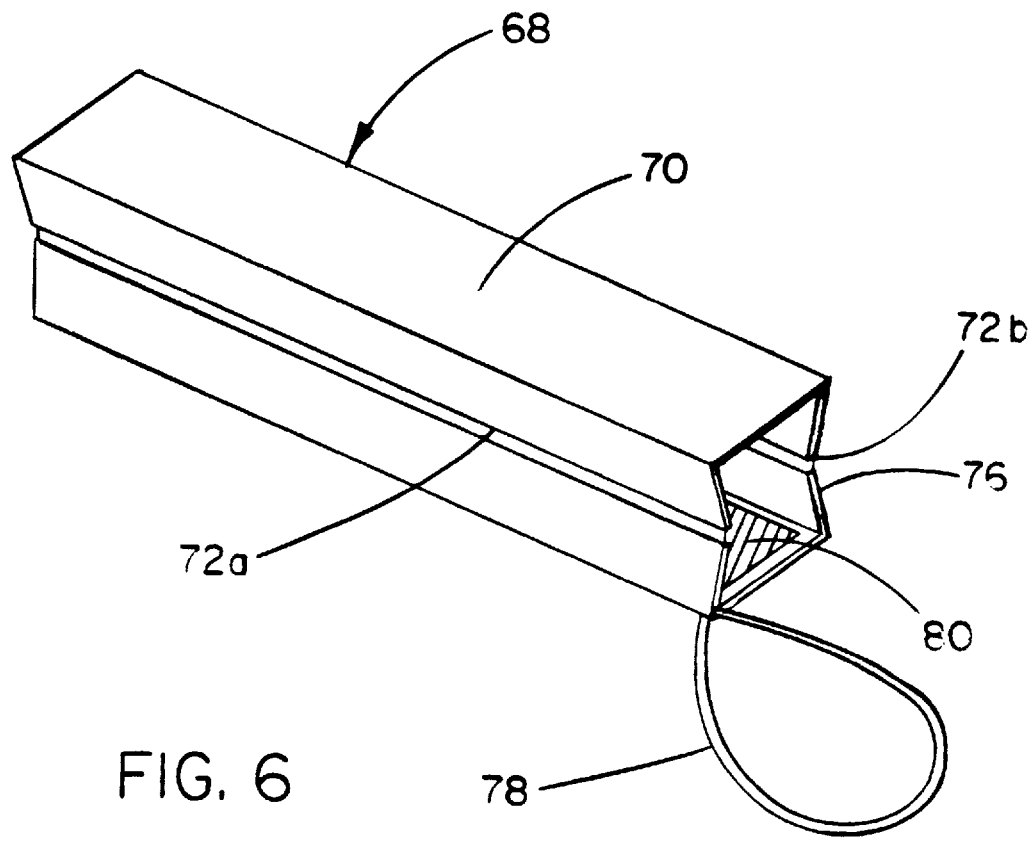
FIG. 6 is a three-quarter isometric view of yet another embodiment of a staple reinforcement device of the present invention.

FIG. 6 illustrates two examples of means to adhere a sleeve 68 to a stapler for ease in extraction from a surgical site. The sleeve 68 shown is essentially rectangular and includes an operative face 70 and two tear lines 72a, 72b. That portion of the sleeve opposite the operative face 70, referred to as a remainder or excess portion 76, includes both a tether 78 and a self-adhesive strip 80 to assist in anchoring the sleeve 68 to a stapler arm. The tether 78 is adapted to attach to the stapler arm, preferably to a clip or similar device provided thereon, and the adhesive strip is adapted to attach to the back of the surgical arm. In operation, once the operative face 70 is attached to the surgical site and the tear lines 72 are separated, the remainder portion 76 is simply extracted from the surgical site by removing the surgical stapler arm. It should be understood that stapler arm attachment methods such as these may be employed alone or in combination with each other to effectuate remainder portion removal from a surgical site.

The exact shape and dimensions of the device of the present invention is a function of the particular constraints of the surgical apparatus and procedures with which it is to be employed. As such, the reinforcement device of the present invention may be formed in virtually any shape or size, including cross-sections comprising a circle, semi-circle, oval or other oblong shape, triangle, rectangle, pentagon, hexagon, etc., or some less defined shape. As has been noted, the face or faces and side/back wall(s) of the device need not be entirely planar, and may include folds or other essentially concave or convex orientations. In fact, folds or concave wall structure may be useful on some or all of the faces or walls of the device in order to assure more secure grip of the stapler arms by the sleeve.

While devices of the present invention may be provided in plethora of different shapes and sizes to fit different types of surgical stapler arms, it is believed that the device of the present invention particularly lends itself to use with means to hold the device on a variety of different stapler arm sizes and shapes. It has been explained that the walls or faces of the device may be bent concave inward (i.e., with a sharp or smooth fold) to provide improved gripping action and greater accommodation of different sizes and shapes of stapler arms.

For greater security, it may also be possible to secure a slightly oversized reinforcement device to a stapler arm using suture, elastic material, or similar means that will retain the reinforcement device in place until activation of the stapler. Such means may be applied by the surgical team at the time of use, or may be pre-installed on the device.

Figure 3:
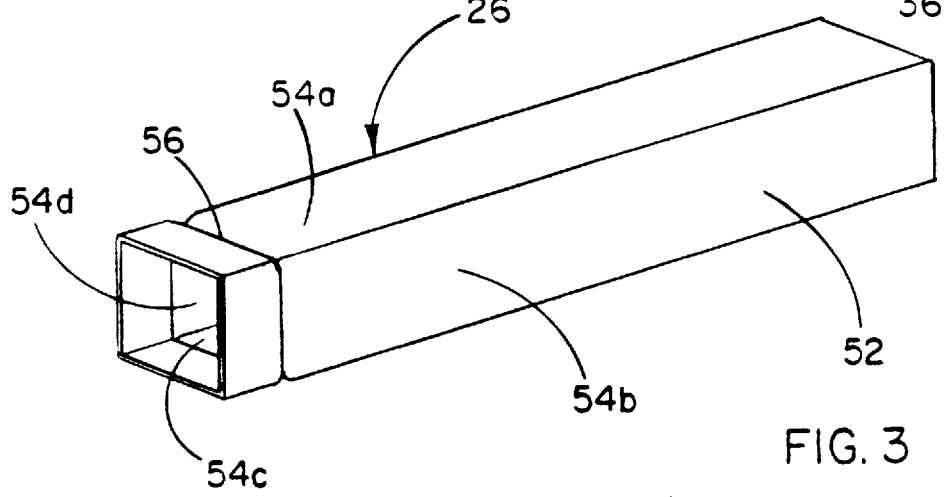
FIG. 3 is a three-quarter isometric view of another embodiment of a surgical staple reinforcement device of the present invention.

Shown in FIG. 3 is one example of how a supplemental attachment means may be incorporated into the device by the manufacturer. This device 26 is again essentially a rectangular sleeve 52 having four operative faces 52a, 52b, 52c, 54d. Toward one end of this device 26, a constrictive device 56 is provided. When the device is installed over a stapler arm, this constrictive device 56 serves to grip the arm and assist in holding the sleeve 52 in place. Suitable constrictive devices for use with the present invention include: essentially non-elastic materials, such as sutures or thin wires; elastic materials, such as natural or synthetic rubbers; mechanical or chemical means to reduce the cross-section of the sleeve in the area where gripping is desired (e.g., forming a fold in the sleeve and then using clips, adhesives, etc., to hold the fold in place); etc. Particularly preferred is a constrictive device that is at least somewhat elastic, such as an elastomeric band adhered to the sleeve, allowing for easy installation of the device on a wider variety of stapler arms and a surer fit of the sleeve on the arms.

Figure 4:
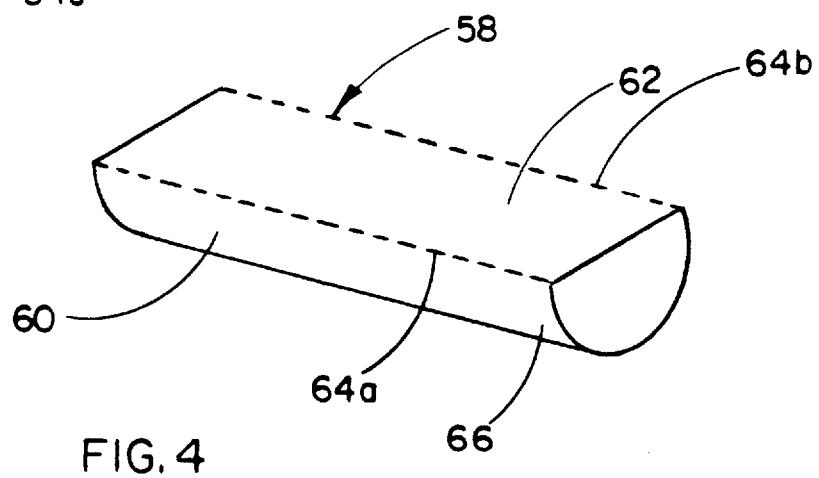
FIG. 4 is a three-quarter isometric view of still another embodiment of a surgical staple reinforcement device of the present invention.

Still another embodiment of a reinforcement device 58 of the present invention is shown in FIG. 4. In this instance, the device 58 comprises a semi-cylindrical sleeve 60, having one relatively planar operative face 62. Perforated tear lines 64a, 64b are provided to allow separation of the operative face 62 from backing material 66. Again, the entire device 58 is formed from implantable material to assure that accidental attachment of undesirable material does not occur.

Without intending to limit the scope of the present invention, the following examples illustrate how it can be made and used.

EXAMPLE 1

A sleeve of the present invention was produced in the following manner.

A fine powder PTFE resin was combined in a blender with an amount of an odorless mineral spirit (ISOPAR M available from Exxon Corporation) until a compound was obtained. The volume of mineral spirit used per gram of fine powder PTFE resin was approximately 0.264 cc/g. The compound was compressed into a billet and extruded through a die attached to a ram type extruder to form a coherent extrudate. A reduction ratio of 127:1 was used (reduction ratio=cross section area of extrusion cylinder divided by the cross section of the extrusion die).

Figure 7:
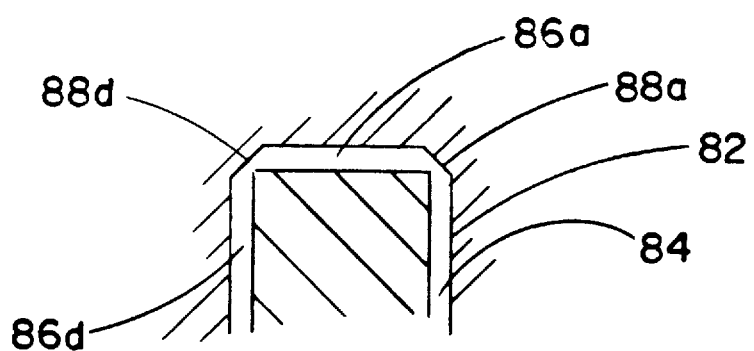
FIG. 7 is a cross-section view an embodiment of an extrusion die suitable for production of one embodiment of a reinforcement device of the present invention.

The die was proportioned to provide finished sleeve having an essentially rectangular cross section with selectively weakened corners. A cross section of this die is shown in FIG. 7. As can be seen the die 82 provides a rectangular gap 84 through which the tube is expanded. The gap has a first thickness of about 0.375 mm along each of operative faces 86a, 86b, 86c, 86d and a second, thinner, thickness of about 0.12 mm at each of corners 88a, 88b, 88c, 88d.

Following extrusion, the odorless mineral spirit was volatilized and removed from the sleeve. Expansion was then performed on the tubular sleeve at a ratio of 2.18:1 at an expansion rate of about 1000% per second. Expansion was performed in a hot oven at a temperature of about 300° C. The sleeve was then subjected to an amorphous locking step by exposing the sleeve to a temperature of about 350° C. for about 70 seconds.

The resulting sleeve had the following properties:

Average fibril length of 2–5 micron

Expansion/stretch ratio of 2.18:1

Longitudinal strength of about 15–20 Kg

Transverse strength of about 5–10 Kg

Operative face thickness of about 0.375 mm

Corner (tear line) thickness of about 0.12 mm

EXAMPLE 2

Sleeves made in accordance with Example 1 were mounted one on each of two arms of a anastomotic surgical stapler. The stapler was then used to perform a lung volume reduction procedure on a test animal. The sleeves proved easy to mount, and to cut and staple through. Following attachment of each of two sets of sleeves, the backing material was easily removed from the attached portions of the sleeve merely by ripping the sleeves along the tear lines using forceps to apply transverse tension. Separation occurred easily and only minimal shredding of the expanded PTFE material occurred along the tear lines.

After a series of incisions were made in this manner, the entire lung was submerged in saline solution to test for air leakage at or around the staples or the staple reinforcement material. No air leakage could be detected.

The present invention can be used in a host of surgical procedures. Among the possible usage are: various lung resection procedures (e.g., blebectomies, lobectomoies, bullectomies, wedge resections, and lung reduction procedures, such as those used to treat symptoms of emphysema); treatment of soft tissue injuries and defects (e.g., abdominal or thoracic wall procedures, gastrointestinal procedures), and as a tool in a variety of other surgical procedures (e.g., reproductive organ repair procedures, etc.). The device may be used with either anastomotic staplers or nonanastomotic staplers. Naturally, the device of the present invention may be used in conjunction with operations on both humans and animals.

It should be appreciated that while the device of the present invention may be used in pairs, as shown in FIG. 5, it is believed that it may also be beneficial to use it to reinforce only one side of certain procedures. For example, the device may be installed on only one side of a surgical seam joining tissue or devices where a weak material is being attached to a relatively strong material (i.e., certain relatively weak tissue or prosthetic devices that may be prone to tear along staple lines may be attached to relatively strong tissue or devices that are not so inclined to tear). In these instances, a device of the present invention can be provided to cover only the material prone to staple damage. Without compromising seam integrity, this allows for a thinner overall seam and reduces the amount of material placed in the patient.

It should be noted that various other materials may be added to the staple reinforcement device of the present invention to provide additional utility. For example, an antimicrobial or antibiotic agent may be coated on and/or filled within the porous structure of the sleeve to provide assistance in avoiding infection. This is considered to be particularly useful in various procedures (e.g., intestine resections, surgery on trauma injuries (e.g., chest or abdominal trauma), etc.) where microbial or bacterial infection is likely. Other useful additives may include adhesives, radio-visible compounds, clotting agents, agents promoting healing, cancer treating agents, etc.

Figure 8:
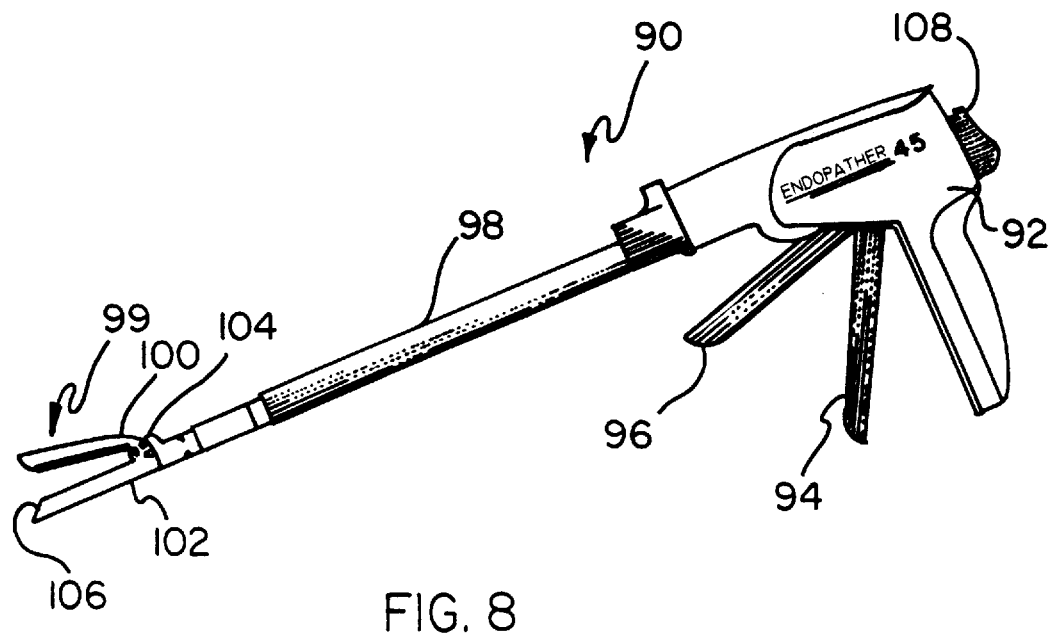
FIG. 8 is a side elevation view of a commercially available endoscopic stapler device.

As has been noted, there are particular concerns related to employing the present invention on an endoscopic stapler device. Shown in FIG. 8 is a typical endoscopic stapler 90, this one being an ENDOPATH thoracic endoscopic liner cutter (Model EZ45) available from Ethicon Endo-Surgery. It should be appreciated that this device is only being used as an example and the present invention may be effectively employed on a variety of makes and models of endoscopic staplers.

An endoscopic stapler 90 typically comprises a handle 92, a closing trigger 94, a firing trigger 96, an extended staff 98, and a stapler head 99. The stapler head 99 comprises a first jaw 100, a second jaw 102, connected together at a pivot 104. One or both of the jaws move around the pivot 104 to allow the jaws 100, 102 to be closed together around tissue to be cut and sealed. In one of the jaws (in this instance, the second jaw 102) is a cartridge 106 containing staples to be fired through the tissue. The opposite jaw (in this instance, the first jaw 100) is an anvil adapted to bend the staples into correct position. In the stapler 90 shown, a jaw release button 108 is provided on the handle 92 to assure that the stapler jaws can be opened only at the appropriate time.

There are a number of problems unique to endoscopic stapler applications. First, fouling of the pivot 104 in the head 99 is a concern. The fact that the head 99 is more compact than the arms on a conventional stapler (such as that illustrated in FIG. 1), there is a much greater possibility that tissue will be caught at the pivot 104. This can lead to fouling of the pivot, which can disrupt proper operation of the device. This problem is exacerbated by the fact that the endoscopic stapler is operated remotely in the body, making exact positioning and tissue manipulation much more difficult.

Second, the remote nature of the device is also a problem with regard to providing a reinforcement sleeve. While individual sleeves can be provided for each of the jaws, the smaller nature of the jaws combined with the fact that the stapler must be operated remotely makes secure attachment of the sleeves to the jaws a significant concern. Friction fit of individual sleeves on each of the jaws separately may by sufficient for many applications, but surgeons generally require greater assurance that the sleeves will not accidentally fall off while manipulating the stapler within a patient.

Third, as can be seen in FIG. 8, the dimensions of the first and second jaws are often asymmetric, with the jaw holding the cartridge 106 generally being larger than the anvil jaw. This difference in size contributes to the difficulty of relying on friction fit alone to hold a reinforcement sleeve in place, requiring two different sized sleeves for each stapler model.

Figure 9:
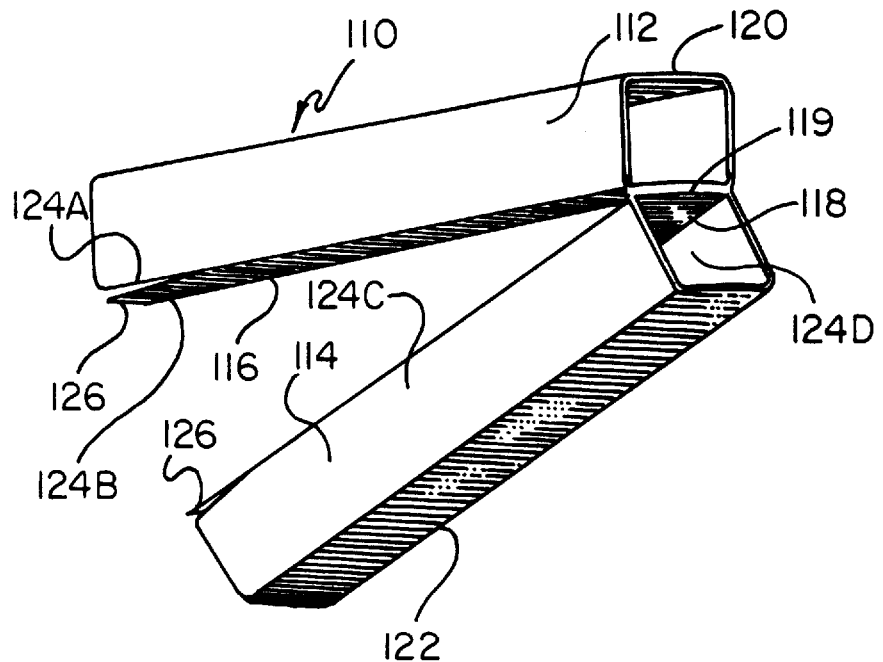
FIG. 9 is a three-quarter isometric view of an endoscopic staple reinforcement device of the present invention.

These problems are all addressed by an endoscopic reinforcement sleeve 110 of the present invention as illustrated in FIG. 9. The endoscopic sleeve 110 comprises a first sleeve element 112 adapted to slide over one of the first stapler jaw 100, and a second sleeve element 114 adapted to slide over the other stapler jaw 102. In the preferred embodiment illustrated, each of the sleeve elements 112, 114 comprises an essentially rectangular shape, generally matching in size and shape the jaws 100, 102. Each of the sleeve elements 112, 114 includes an operative face 116, 118, respectively, through which staples are attached.

The two sleeve elements 112, 114 are connected together by a hinge 119 connecting the operative faces 116, 118. The hinge 119 may be constructed through a variety of methods, including forming the two operative faces 116, 118 from the same continuous strip of material, or by adhering two or more separate pieces of material together to form a connection between the two sleeve elements 112, 114.

Each of the sleeve elements 112,114 includes backing material 120, 122, respectively, adapted to hold each sleeve element on the jaws. As was true with the embodiments of reinforcement sleeves previously described, it is desirable to include tear lines 124a, 124b, 124c, 124d on the sleeve elements to assist in separation of the backing material 120, 122 from the operative faces 116, 118 once installed in the patient. Again, cuts 126 may be provided on the tear lines 124 to assist in the separation process.

The construction of the reinforcement sleeve in this manner has numerous advantages over other sleeve constructions for endoscopic applications. First, as a segment of material blocking access to the pivot 104, the hinge 119 provides a barrier to tissue migration into the pivot 104. As such, the likelihood of fouling or other contamination is greatly diminished when operating the stapler. Second, the hinge 119 provides an excellent mechanism to help hold the sleeve in place during manipulation within a patient. As is explained in greater detail below, with the use of the endoscopic sleeve 110 the two sleeve elements 112, 114 can be merely slid over the jaws 100, 102, with only a minimal friction fit required on at least one of the jaws. The fact that the two sleeve elements are attached together at the hinge 119 provides very secure retention of the sleeve 110 on the jaws during manipulation. This is particularly true when the jaws are separated from one another—a time when individual sleeves would be extremely prone to falling off the jaws.

Figure 10:
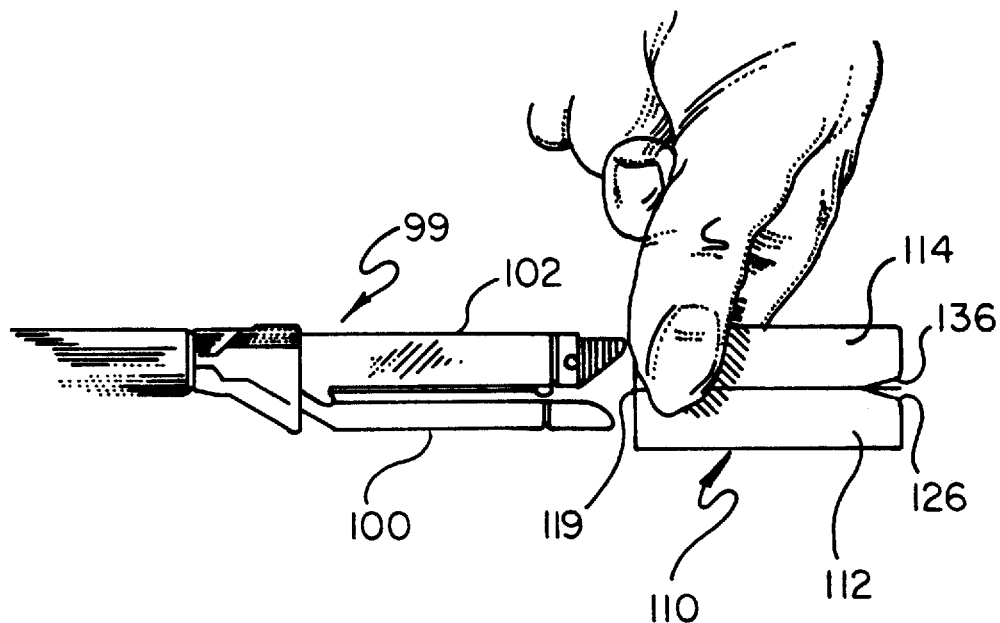
FIG. 10 is a side elevation view of a endoscopic staple reinforcement device of the present invention being mounted on endoscopic stapler jaws.
Figure 11:
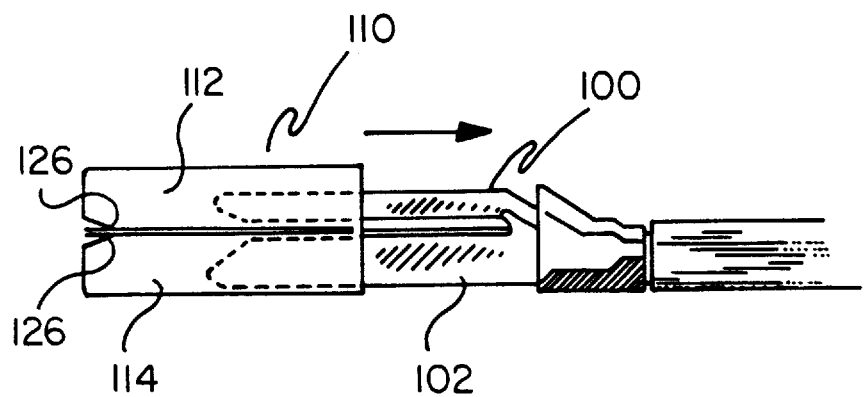
FIG. 11 is a side elevation view of the endoscopic staple reinforcement device of the present invention being slid over endoscopic stapler jaws.
Figure 12:
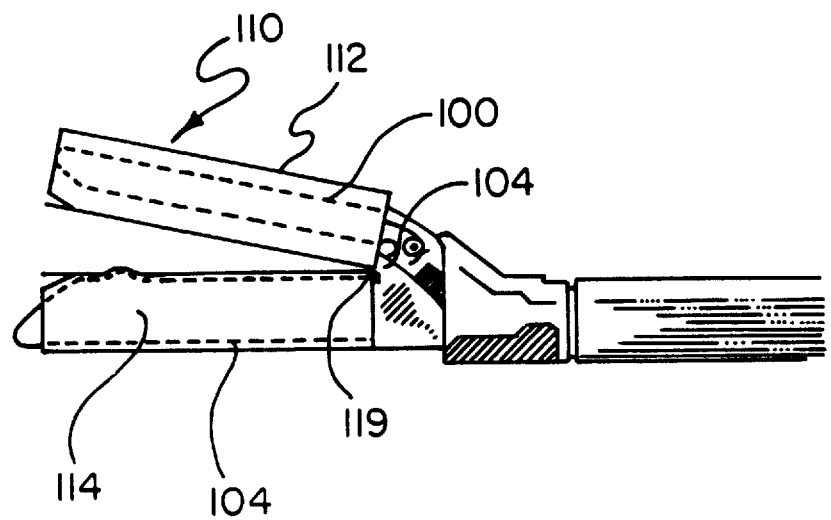
FIG. 12 is a side elevation view of the endoscopic staple reinforcement device of the present invention fully mounted on endoscopic stapler jaws, the jaws shown in an open position.

The installation of the endoscopic sleeve 110 of the present invention is illustrated in FIGS. 10 through 12. As is shown in FIG. 10, the sleeve 110 is placed in a folded position around hinge 119, with each of the sleeve elements 112, 114 aligned with each of the jaw members 100,102. From this position the sleeve 110 is simply slid onto the jaw members 100,102 as is shown in FIG. 11. As is shown in FIG. 12, once installed on the stapler head 99, the hinge 119 will abut the pivot point 104 of the stapler. This provides an effective shield to keep tissue from fouling the pivot point 104. Additionally, the hinge 119 assures that the sleeve 110 will not separate from the stapler head 99 when the jaws 100, 102 are in an open position, as shown.

Figure 13:
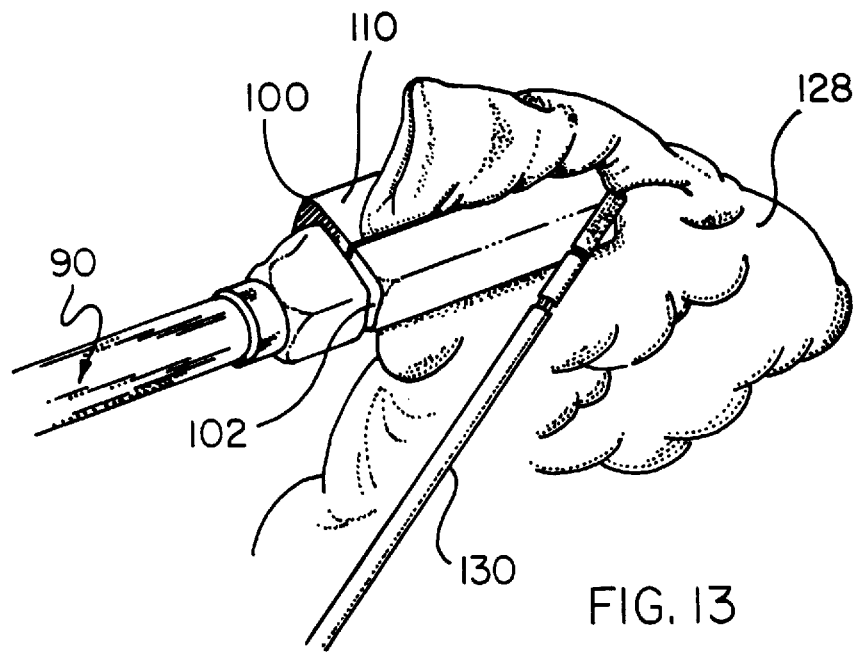
FIG. 13 is a three-quarter isometric view of the endoscopic staple reinforcement device of the present invention shown clamped in place around tissue, with endoscopic stapler jaws shown in a closed and locked position.
Figure 14:
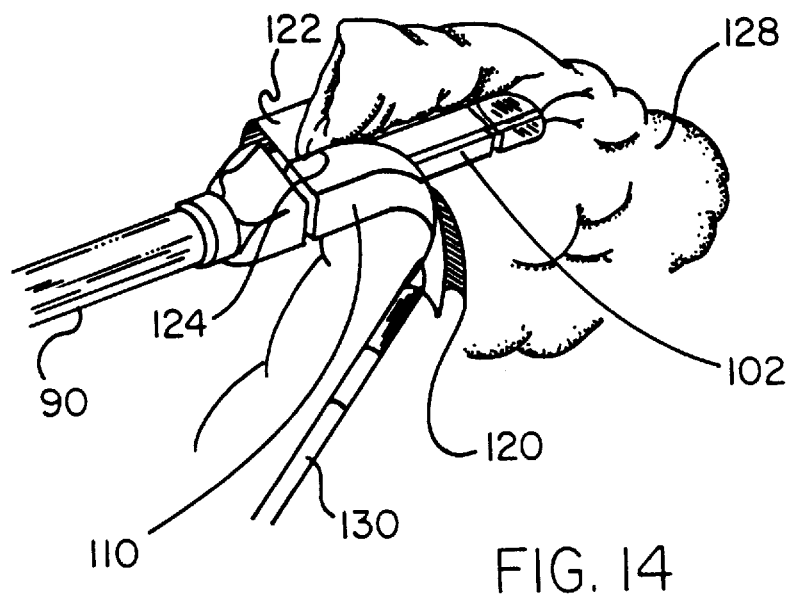
FIG. 14 is a three-quarter isometric view of the endoscopic staple reinforcement device and endoscopic stapler jaws shown in FIG. 13, with excess material being removed from the surgical site.
Figure 15:
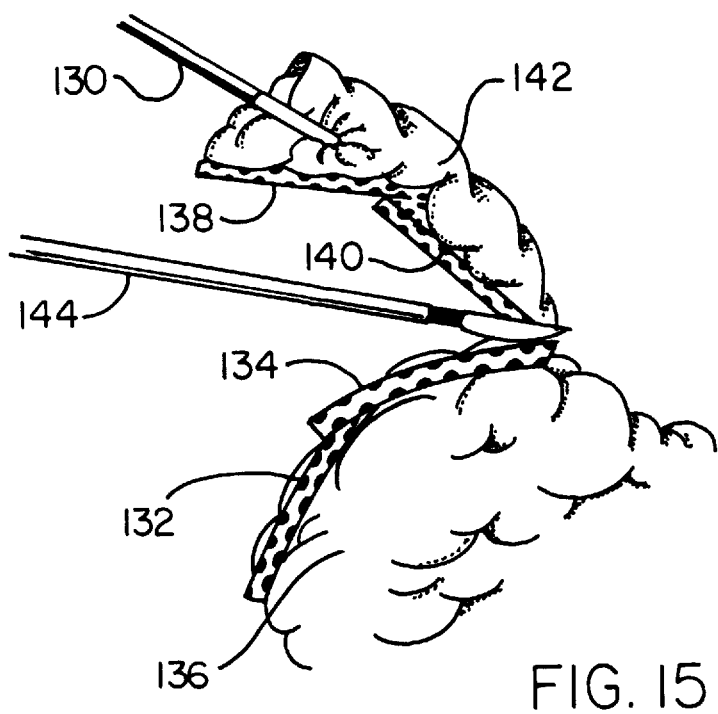
FIG. 15 is a three-quarter isometric view of tissue having been cut and sealed using an endoscopic stapler and the reinforcement device of the present invention.

The operation of the endoscopic reinforcement sleeve of the present invention is illustrated in FIGS. 13 through 15. FIG. 13 shows an endoscopic stapler 90 with its jaws 100,102 closed around lung tissue 128. The endoscopic reinforcement sleeve 110 of the present invention is mounted on each of the jaws 100, 102. An endoscopic forceps 130 is attached to the sleeve 110 to assist in the removal of excess sleeve material following attachment.

As is shown in FIG. 14, following actuation of the stapler 90 to cut and seal the tissue, the backing material 120 can be removed by peeling it away from the operative faces along the tear lines 124. This procedure is repeated on the opposite stapler jaw to remove that backing material 122.

As is shown in FIG. 15, by performing this procedure repeatedly a series of reinforced staple seams 132, 134 are created in healthy tissue 136 as well as a series of reinforced staple seams 138, 140 in excised tissue 142. The excised tissue 142 can then be readily removed from the surgical site using a forceps 130 and, if required, scissors or scalpel 144 if needed to finish separation.

The endoscopic reinforcement sleeve 110 may be formed from any appropriate shape and size of material. Ideally each of the sleeve elements 112, 114 should be proportioned to generally match the shape and size of the stapler jaws, so as to provide a friction fit thereon (being slightly larger than the jaws to allow the sleeve to easily slide on to the jaws). To match most endoscopic staplers, the sleeve is preferably generally rectangular in cross–section. Again, it is preferable that the backing material have somewhat conceived side walls to assist in holding the sleeve in place on the stapler.

For ease in construction, the sleeve 110 may be formed form a single tube of material that is cut midway along its length to form the two sleeve elements 112, 114 and leaving a continuous operative face 116, 118 connecting the two elements at the hinge 119. This allows the device to be readily fashioned from a continuous tube of material with only minimal preparation required to form the final product.

Alternatively, the endoscopic reinforcement sleeve may be formed from two or more separate components that are attached together. Attachment of the separate components together may be accomplished through any of a variety of methods, including without limitation using: adhesive, heat or ultrasonic welding, suture, etc. While separate elements are more difficult to assemble, improved properties can be provided through this method, such as: providing different sized sleeve elements (i.e., proportioning each of the sleeve elements to better fit asymmetric sized jaws); providing sleeve elements, or portions of sleeve elements, with different properties (e.g., texture, thickness, stiffness, surface treatments, etc.); providing sleeves that are composites of different materials; etc.

The endoscopic reinforcement sleeve described herein is primarily intended for use on an endoscopic stapler device. However, it should be appreciated that a reinforcement sleeve having two sleeve elements and a connecting hinge may also be applied to conventional surgical staplers having a pivoted connection between the stapler arms. As such, the terms "jaws" and "arms" are intended to be used interchangeably herein to signify the stapler members used to surround and apply staples through tissue or other material.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A reinforcement sleeve for a surgical stapler device comprising:

a first sleeve element adapted to attach to a first jaw member of the surgical stapler;

a second sleeve element adapted to attach to a second jaw member of the surgical stapler; and a hinge connecting the first sleeve element to the second sleeve element.

2. The reinforcement sleeve of claim 2 wherein each of the first and second sleeve elements comprises an operative face attached to backing material.

3. The reinforcement sleeve of claim 2 wherein the operative faces of the first and second sleeve elements comprise a continuous length of material connecting the first and second sleeve elements together to form the hinge.

4. The reinforcement sleeve of claim 2 wherein the operative faces of the first and second sleeve elements comprise a length of a single material.

5. The reinforcement sleeve of claim 1 wherein the first sleeve element, the second sleeve element, and the hinge all comprise the same material.

6. The reinforcement sleeve of claim 1 wherein each of the sleeve elements comprises an essentially rectangular cross section.

7. The reinforcement sleeve of claim 1 wherein the surgical stapler comprises an endoscopic stapler having a pivot connecting the first and second jaw members; and the hinge comprises a segment of material that protects the pivot from contamination during use.

8. The reinforcement sleeve of claim 1 wherein the first and second sleeve elements each comprises an essentially rectangular cross section;

the first and second sleeve elements and the hinge all comprise the same material.

9. The reinforcement sleeve of claim 8 wherein the first and second sleeve elements and the hinge all comprise polytetrafluoroethylene.

10. The reinforcement sleeve of claim 8 wherein the sleeve comprises a single piece of material.

11. The reinforcement sleeve of claim 8 wherein the surgical stapler comprises an endoscopic stapler having a pivot connecting the first and second jaw members; and the hinge comprises a segment of material that protects the pivot from contamination during use.

12. The reinforcement sleeve of claim 1 wherein each of the sleeve elements comprises an operative face attached to backing material; and means are provided to allow the backing material to be easily separated from the operative face.

13. The reinforcement sleeve of claim 12 wherein the operative face and backing material comprise the same material; and the means to allow the backing material to be separated from the operative face comprises tear lines.

14. A method for applying surgical staples to a surgical site so as to reinforce the surgical site, which comprises providing a surgical stapler having a pair of jaw members connected at a pivot, the jaw members being adapted to move from a closed position whereby the jaw members abut one another and an open position whereby the jaw members are separated from one another around the pivot;

providing a sleeve of reinforcement material, the sleeve comprising first and second sleeve elements, each adapted to be attached to one of the pair of jaw members, and a hinge connecting the two sleeve elements together, wherein each of the sleeve elements includes an operative face through which staples are applied and wherein the sleeve is adapted to slide over the pair of arm;

placing the jaw members in the closed position and sliding the sleeve over the jaw members arm so as to position the operative faces to receive surgical staples and so as to position the hinge to abut the pivot;

placing the jaw members in the open position and orienting the stapler over the surgical site, the sleeve being held to the surgical stapler at least in part by the hinge connecting the two sleeve elements;

applying surgical staples through the surgical site and the operative faces of the sleeve, the sleeve providing reinforcement to prevent tearing of the surgical site.

15. The method of claim 14 that further comprises each sleeve element having backing material attached to the operative face, the backing material assisting in holding the sleeve element on the jaw;

trimming the sleeve of the backing material following applying the surgical staples through the operative face.

16. The method of claim 15 that further comprises providing as each sleeve element an operative face and backing material formed from the same material;

providing each sleeve element with tear lines allowing ready separation of the operative face of the sleeve from the backing material; and trimming the sleeve of the backing material by separating along the tear lines.

17. The method of claim 14 that further comprises providing as the hinge a segment of material that serves as a barrier to tissue movement into the pivot;

positioning the hinge against the pivot so as to protect the pivot from contamination.

* * * * *

UNITED STATES PATENT AND TRADEMARK OFFICE
CERTIFICATE OF CORRECTION

PATENT NO. : 5,810,855  
DATED : September 22, 1998  
INVENTOR(S) : Rayburn et al.

Page 1 of 1

It is certified that error appears in the above-identified patent and that said Letters Patent is hereby corrected as shown below:

Title page,
Item [22], Filed: "Jul 11, 1997" should read -- Jul. 9, 1997 --

Column 15,
Line 25, The reinforcement sleeve of claim "2" should read The reinforcement sleeve of claim -- 1 --

Signed and Sealed this

Fourteenth Day of May, 2002

*Attest:*

JAMES E. ROGAN
*Attesting Officer*  *Director of the United States Patent and Trademark Office*